United States Patent [19]

Sethi et al.

[11] Patent Number: 4,891,120
[45] Date of Patent: Jan. 2, 1990

[54] CHROMATOGRAPHIC SEPARATION DEVICE

[76] Inventors: Rajinder S. Sethi, 38 Norman Road, Northampton, Great Britain, NN3 2SG; Jack Brettle, 7 Clavert Road, Green Norton, Towcester, Northampton; Christopher Lowe, The Limes, Hempstead, Saffron Waldon, Essex, both of Great Britain

[21] Appl. No.: 175,389
[22] PCT Filed: Jun. 8, 1987
[86] PCT No.: PCT/GB87/00393
§ 371 Date: Apr. 12, 1988
§ 102(e) Date: Apr. 12, 1988
[87] PCT Pub. No.: WO87/07953
PCT Pub. Date: Dec. 30, 1987

[30] Foreign Application Priority Data

Jun. 6, 1986 [GB] United Kingdom ................. 8613785

[51] Int. Cl.⁴ ..................... G01N 27/26; G01N 30/02; G01N 30/62; G01N 30/64
[52] U.S. Cl. .................................. 204/299 R; 73/23.1; 73/61.1 C
[58] Field of Search ........................... 73/23.1, 61.1 C; 204/299 R

[56] References Cited

U.S. PATENT DOCUMENTS

| | | | |
|---|---|---|---|
| 3,149,941 | 9/1964 | Barnitz et al. | 73/23.1 X |
| 3,465,884 | 9/1969 | Matherne | 210/658 X |
| 3,503,712 | 3/1970 | Sussman | 73/23.1 X |
| 3,538,744 | 11/1970 | Karasek | 73/23.1 |
| 3,932,264 | 1/1976 | Haruki et al. | 204/299 R |
| 4,462,962 | 7/1984 | Baba et al. | 422/20 X |
| 4,471,646 | 9/1984 | Jerman et al. | 73/23 |
| 4,474,889 | 10/1984 | Terry et al. | 73/23.1 X |

FOREIGN PATENT DOCUMENTS

| | | | |
|---|---|---|---|
| 1113319 | 8/1961 | Fed. Rep. of Germany | 73/23.1 |
| 0230058 | 11/1985 | Japan . | |
| 922648 | 4/1963 | United Kingdom | 73/23.1 |

OTHER PUBLICATIONS

Terry, S. C. et al., "A Column Gas Chromatography System on a Single Wafer of Silicon" Des. Biomedical Appl. Solid State Chem. Sens. Workshop 1977.
Malir, K. et al., "Mass Flow Meter" IBM Technical Disclosure Bulletin, vol. 21, No. 8, Jan. 1979.
Svoboda, V. et al., "A Conductimetric Detector with a Wide Range for Liquid Chromotography" Journal of Chrom. 148 (1978) pp. 111–116.
Pecsok, R. et al., "A Sensitive Low Volume Detector for Liquid Chromatogrpahy" Analytical Chemistry, vol. 40, No. 11, Sep. 1968.
Foret, F. et al., "On-Line Fiber Optic UV Detection Cell and Conductivity Cell for Capillary Zone Electrophoresis" Electrophoresis 1986, 7, pp. 430–432.

*Primary Examiner*—John F. Niebling
*Assistant Examiner*—John S. Starsiak, Jr.
*Attorney, Agent, or Firm*—Fleit, Jacobson, Cohn, Price, Holman & Stern

[57] ABSTRACT

A chromatographic separation device comprises a body 2 of a semiconductor material which body has a longitudinal channel 1 formed in a surface thereof, the channel 1 being capable of containing a predetermined volume of a liquid or solid material for a chromatography test or separation procedure, the channel carrying at least one electrode 6 positioned intermediate the channel ends. The semiconductor body may additionally support an electronic or optical sensor 8 arranged in line with said channel 1 to provide an integrated detection system.

8 Claims, 3 Drawing Sheets

CHROMATOGRAPHIC SEPARATION DEVICE

This invention relates to a chromatographic separation device. It relates particularly to the provision of such a device that can be used for a variety of applications such as electrolysis, chromatography, electrophoresis and the study of electrokinetic phenomena.

The development of separation technology has brought with it the need to be able to work accurately with very small test samples and possibly to provide a separation cell that can be integrated with a detection system. The signals from an integrated sensor will be less likely to be influenced by noise or leakage as compared with those of a discrete sensor. The sensing element would thus make use of a non-specific technique such as conductivity, optical (absorbance, refractive index) or electrochemical properties or, more likely, a suitable combination of these.

The present invention was devised to provide a separation device that was capable of being manufactured in a miniature form to assist the microseparation and detection of biochemical and other chemical species.

According to the invention, there is provided a chromatographic separation device comprising a body of a semiconductor material which body has a longitudinal channel formed in a surface thereof, the channel being capable of containing a predetermined volume of a liquid or solid material for a chromatographic test or separation procedure, the channel carrying at least one electrode positioned intermediate the channel ends.

Preferably, an open side of the said channel is closed by a cover plate.

The channel may be formed by an integrated circuit technique such as photolithography and micromachining. Alternatively, the channel may be formed by a micromechanical machining technique such as electromechanical sawing.

The body of semiconductor material may be a silicon wafer. The separation device may further carry an electronic or optical sensor element which is located in line with the channel. The body of semiconductor material may be provided with two or more of the longitudinal channels, the channels being located in a mutually parallel arrangement. By way of example, some particular embodiments of the invention will now be described with reference to the accompanying drawings, in which.

Figure 13:
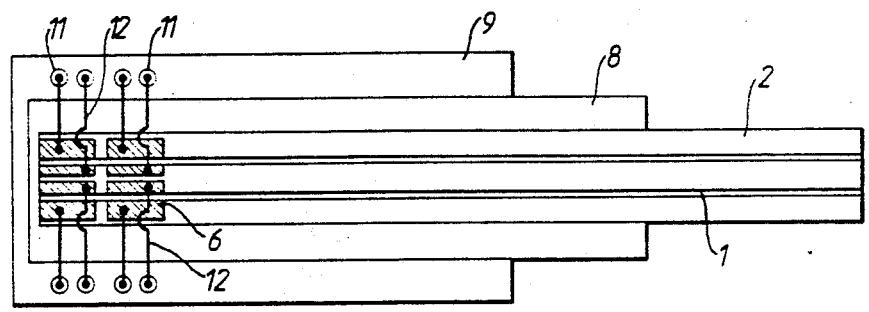
Figure 14:
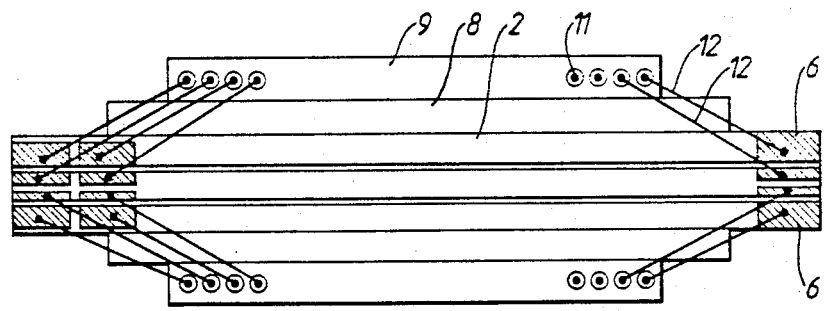

FIG. 13 is a plan view showing a prototype construction of a single ended chromatographic separation device; and, FIG. 14 is a similar view of a double ended separation device. The construction of the chromatographic separation device of the invention begins with the preparation of a slice of semiconductor material and in the embodiment about to be described this was a silicon wafer. For convenience in use of the separation device some of the test slices were formed with two channels located in a mutually parallel arrangement.

The formation of very narrow channels in silicon wafer material can be achieved by using the well-developed integrated circuit technology of photolithography, micromachining or micromechanical machining. Micromachining utilises the controlled etching characteristics of silicon, and involves anisotropic and isotropic wet and/or dry etching. Anisotropic etchants, which are also known as orientation-dependent or crystallographic etchants, etch silicon at different rates in different directions in the crystal lattice; they can form a variety of well-defined shapes with sharp edges and corners. Typical examples include hot alkaline solutions such as aqueous potassium hydroxide (KOH) or sodium hydroxide and a mixture of ethylendiamine, pyrocatechol and water known as EDP. Dry etching techniques such as reactive ion etching and argon ion beam milling can also be employed to perform anisotropic etching. Isotropic etchants, on the other hand, etch the silicon crystal at the same rate in all directions and generally produce rounded shapes. Typical examples include mixtures of hydrofluoric, nitric and acetic acids known as HNA.

The fabrication of the channel structures by micromachining involved the following main steps: formation of a layer of silicon dioxide on the silicon wafer body by a standard thermal oxidation process; definition of patterns on the oxidised surface by using standard photoresist and photolithography processes; removal of oxide by wet or dry etching where channels were to be formed thus exposing the silicon surface; removal of photoresist and etching the silicon body in places where it was unprotected by the oxide mask. In structures requiring long etching times, silicon nitride was generally employed as a masking material in place of silicon oxide ($SiO_2$). In certain cases, gold and chromium metals might alternatively be employed for this purpose.

Anisotropic wet etching was performed mainly on silicon wafers with two alternative types of crystal surface orientations namely $<100>$ and $<110>$. Etching along $\{110\}$ planes was quite rapid compared with $\{100\}$ planes. The attack along a $\{111\}$ plane was extremely slow, if it occurred at all, by the action of anistropic etchants. A variety of channels was formed by controlling orientation, shape and size of the oxide openings on the surface of these wafers, and etching silicon with standard anisotropic etchants mentioned earlier. When etching with these etchants, proper mask alignment with specific crystallographic axes of the wafer was considered of utmost importance if the required structures were to be precise. Some typical cross-sectional profiles of channels etched in this way in silicon for utilising in chromatographic and electrophoretic devices are described below.

Figure 1:
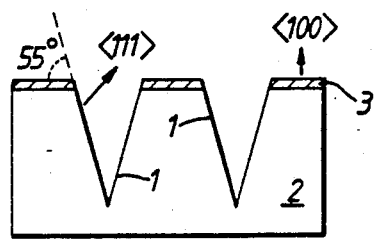
FIG. 1 is a cross-sectional view greatly enlarged of an anisotropically etched microchannel structure in a body of silicon wafer material.
Figure 2:
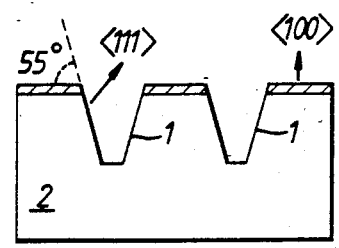
FIG. 2 is a similar view showing a different channel shape.
Figure 3:
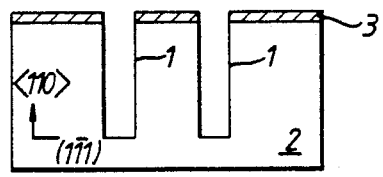
FIG. 3 is a similar view showing the result of etching a body of silicon having a different crystal orientation.

As shown in FIG. 1, V-shaped channels 1 were formed in a silicon wafer body 2 by an alkaline etchant (KOH) acting through rectangular openings in an oxide mask 3 oriented along the <110> direction of a <100> wafer with {111} side walls. Etching was stopped in the early stages to produce the structure shown in FIG. 2. In the formation of narrow channels, the depth needed to be closely controlled by the width of the openings in the oxide etch mask. For producing deeper structures (greater than 50 microns), silicon nitride was employed as the masking material. Electrochemical etching was also employed to reduce the problem of undercutting the mask. In a <110> oriented wafer, two sets of {111} planes are aligned perpendicular to the (110) surface plane although not to each other. Long, deep and closely spaced channels, with vertical wall {111} side terminations (FIG. 3), were etched by potassium hydroxide reagent in a <110> silicon wafer; the etching ratio in the <110> to <111> direction was very high (this ratio being about 400 to 1).

Figure 4:
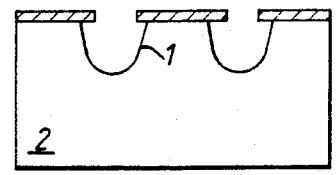
FIG. 4 is a similar view showing the result of an isotropic etching process.
Figure 5:
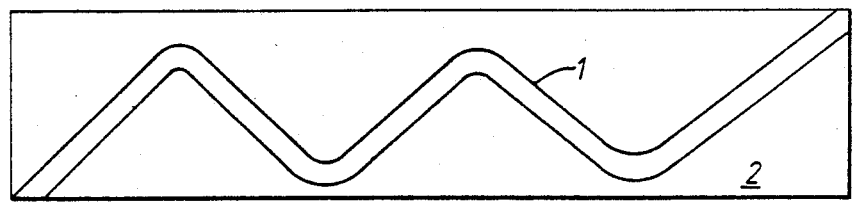
FIG. 5 is a plan view showing the formation of a channel having a serpentine shape by the etching process.

An isotropic etchant (HNA), with continuous agitation, was employed to produce the channel structures shown in FIG. 4. The HNA etch can be employed to produce a variety of channel structures such as serpentine, spiral, etc. the alignments of which are independent of crystallographic orientations of the silicon wafer material. A plan view of a typical serpentine etched structure is shown in FIG. 5.

Figure 6:
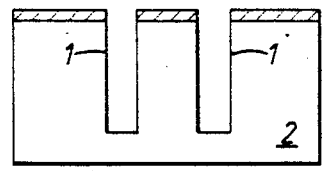
FIG. 6 is similar to FIG. 4 and shows the result of an electromechanical sawing process.

Although rarely used for etching silicon, the technique of micromechanical machining has been found to be suitable as an alternative process for forming the channels. It mainly involves electromechanical sawing with very fine diamond blades under controlled conditions to produce nearly rectangular, closely spaced channels in the silicon. The shapes formed are independent of crystallographic orientation of the silicon wafer. A typical sawed cross section (75 microns ×200 microns) is shown in FIG. 6.

The metal contact electrodes required in the fabrication of electrophoretic devices and for the detection/sensing of species by conductivity and other electrochemical measurements were generally deposited by a standard multimetal sputter deposition process. Four alternative metallisation schemes namely titanium/gold, titanium/platinum/gold, chromium/gold and chromium/platinum/gold were employed for this purpose. The thickness of each of the metals titanium, platinum and chromium was usually around one hundred nanometres whereas that of gold varied between 1 micron to 3 microns depending upon particular design and application. Metal contact patterns were produced either by using standard photoresist, photolithography, metal etching and resist float-off technique or by depositing metals directly through contact ceramic or metal masks. A variety of etched and sawed column structures were electroded; one typical cross section view of such a structure is given in FIG. 7.

Figure 7:
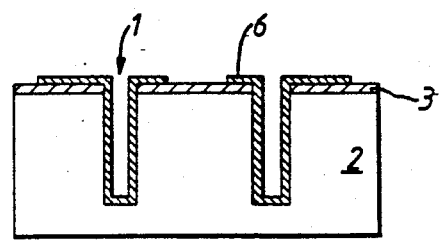
FIG. 7 is a cross-sectional view showing a metal contact pattern deposited on a channel.

As depicted in FIG. 7, the silicon wafer body 2 carries a silicon oxide mask 3 having a thickness of about 0.5 microns and above the channel 1 an electrode 6 area has been deposited. The electrode 6 area covers the two sides of the channel 1 and it also descends down the side walls of the channel and across the channel bottom. The presence of electrode material in the channel is not required because it reduces the cross-sectional area of the channel. Accordingly, this excess electrode material was removed by etching or by the electromechanical sawing operation to leave only the portions of electrode 6 which lie on top of the oxide mask 3.

Figure 9:
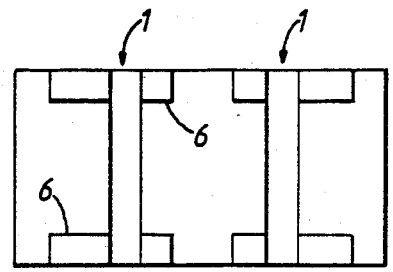
FIG. 9 is a plan view of the electrode structure depicted in FIG. 8.
Figure 8:
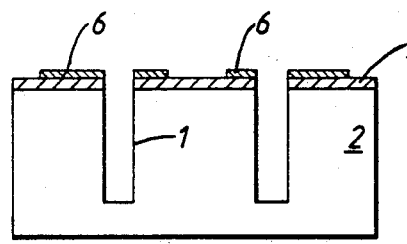
FIG. 8 is a similar view showing the metal contact pattern having been etched or sawed to partially remove the metal deposit.
Figure 10:
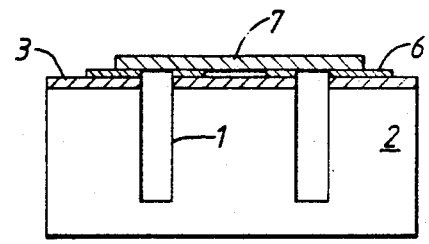
FIG. 10 is a cross-sectional view of the electrode structure on a channel with a cover plate placed over the channel.

The cross-sectional view of the wafer body 2 then appears as in FIG. 8, and a plan view is given in FIG. 9. A view of the wafer body with the cover plate 7 in place is given in FIG. 10.

Figure 11:
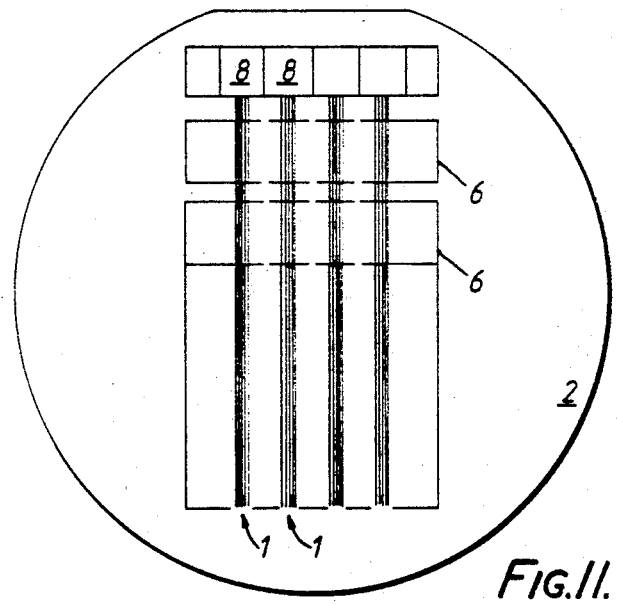
FIG. 11 is a plan view of a silicon wafer provided with four chromatographic separation devices of the invention and an array of electronic or optical sensors.

FIG. 11 gives a plan view of a practical construction in which a circular silicon wafer body 2 having a diameter of three inches forms a substrate for four channels 1 each having a width about 75 microns and a depth of about 200 microns. Each channel 1 has two electrodes 6, the two electrodes being spaced longitudinally along the length of the channel. At the end of each channel 1 there is provided an electronic or optical sensor 8, the four sensors being mounted as an array on the surface of the wafer body 2.

The resulting open channel structures formed by the abovementioned techniques in silicon wafer material were covered over with a Pyrex (Registered Trade Mark) glass cover plate which was merely placed over the open side of the channels or in alternative embodiments was bonded into place anodically or with an adhesive. This produced an enclosed capillary channel structure the dimensions of which could be varied from a fraction of a micron to many microns (about 300 microns). The minimum dimensions of the channels which can be employed in chromatographic devices will be limited by the 'molecular size' of the species under detection whereas in the case of electrophoretic devices these will be mainly controlled by the thickness of the double layer of the species. The nonaqueous systems such as proteins and macromolecules are most likely to have larger values of the double layer thickness (a few orders of magnitude) compared with aqueous systems about 0.5 nanometers.

Use of the chromatographic separation device of the invention is illustrated by the following Examples: EXAMPLE 1 Chromatography in Microchannels and Detection on a Silicon Wafer In a sample of the device corresponding to that shown in FIG. 11, the channels (width about 75 microns, depth about 200 microns) were filled with a 1.5% agarose solution, immobilised and held in place by covering with a glass cover plate. The operation of filling the channel was effected by conventional methods such as diffusion and the application of high pressures. The wafer was placed in a beaker containing a small quantity of the enzyme beta-galactosidase in sodium phosphate buffer solution. The device was then left standing overnight in a vertical position with the lower channel ends just dipping in the solution. The channels were subsequently analysed for enzyme activity using 4-methylumbellifyl-beta-D-galactopyranoside, which is enzymatically cleaved to form a fluorescent product. Under ultraviolet irradiation the channels were seen to fluoresce and it was concluded that the enzyme had migrated up the channels.

Figure 12:
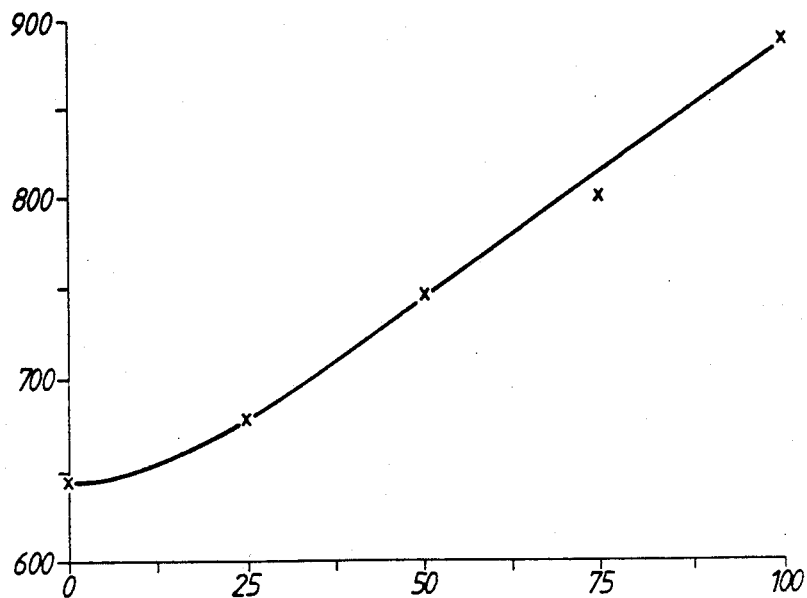
FIG. 12 is a graph showing the results of some conductance measurements made using the separation devices.

To detect the species near the 'exit' end of the channels by conductivity measurements, the above experiment was repeated using sodium phosphate buffer solutions of various concentrations. Agarose was immobilised in the channels as before. The devices were allowed to stand upright in a small volume of sodium phosphate buffer solution, and the conductance between the two metal pad electrodes was then measured. The results are shown in the graph of FIG. 12, where the vertical axis measures conductance (in microsiemens) and the horizontal axis measures concentration (in millimoles) of the relevant sodium phosphate buffer solution. It can be seen that the steady state conductance is linearly related to the ionic strength of the buffer solution.

These two experiments demonstrate that it is possible for biochemical or other chemical species to migrate along these microscopic channels and to be detected fluoroscopically or for the concentration of the migrating chemical to be determined quantitatively by the conductance measurements when using an integrated sensor.

EXAMPLE 2

A Chromatographic Separation and Sensing Device

To construct a practical chromatographic device as shown in FIG. 13, a portion of the silicon wafer body 2 measuring 7.5mm ×65mm and being provided with rectangular channels 1 (dimensions: 100 microns ×200 microns) was mounted using an epoxy resin adhesive onto a an alumina strip 8. The alumina strip 8 measured 13mm 33 50 mm. In turn, the strip 8 was epoxy resin bonded to a gold plated electronics mounting package 9 having insulated pins 11 for making electrical connections. The chromatographic device was then bonded to the pins 11 by means of gold wires 12 attached to the electrode 6 areas.

In tests carried out on the separation and sensing properties of this device, the channels were filled with a variety of chromatographic media for the resolution of gases and volatiles by gas chromatography and a variety of other materials by liquid chromatography. Thus, chromatographic media comprising styrene/divinylbenzene ion exchange resins and acrylic carboxylic, tertiary amino and chelating resins were formed in situ by polymerisation onto an allyldimethyl chlorosilane-activated channel. These media were exploited for the resolution of a variety of charged metallic, organic and proteinaceous species. Similarly, silica or alumina adsorbents comprising oxidised silicon or aluminium channels were used for the micro-chromatography of complex lipids, fatty acids, steroids, alkaloids, phenols, hydrocarbons, dicarboxylic acids, amino acids, esters, peroxides, aldehydes, alcohols and nucleic acids.

Proteins and enzymes were resolved by gel filtration media comprising sephadexes, agaroses, acrylics or porous silicas, by ion exchange on carbohydrate-based or acrylic exchanges, hydrophobic adsorbents such as phenyl or alkyl-agaroses. Selective adsorption of individual proteins or groups of proteins was achieved by microaffinity chromatography on immobilised dyes, lectins, chelating ligands, protein A, boronate, heparin, nucleotides, immunoligands, oligonucleotides and nucleic acids, and appropriate chiral phases for the resolution of isomeric and chiral compounds.

EXAMPLE 3

An Electrophoretic Separation and Sensing Device

In a similar construction to that used for the chromatographic device of Example 2, an electrophoretic device as depicted in FIG. 14 was built. For the electrophoretic device, the electrode 6 areas needed to be provided at both ends of the channels 1, consequently the pins 11 and the gold wires 12 were similarly required to be located at both the ends of the channels 1.

In tests carried out on the separation and sensing properties of the device, it was found that the positioning of the electrodes at the distal ends of the channel 1 filled with an appropriate electrophoretic medium permitted miniaturised electrophoresis to be performed within minutes. For example, electrophoresis in agarose gel resolved proteins according to charge, whilst polyacrylamide gel electrophoresis was found to impose a sieving effect additional to the charge separation. Such a miniaturised device containing agarose or acrylamide gels could be used to resolve proteins, enzymes and isoenzymes in normal and abnormal serum samples.

Similarly, agarose and polyacrylamide gel electrophoresis may be used for the resolution of nucleic acids and oligonucleotides and the device finds particular application in DNA restriction fragment analysis, DNA sequencing and probe analysis. These supports are also applicable to a variety of immunological, electrofocussing and affinity techniques.

The chromatographic separation device of the invention is proposed to be employed to study the electrokinetic or zeta potential, which is involved in electro-osmosis, electrophoresis and allied phenomena. THe zeta potential is the potential between the fixed and freely mobile part of the double layer and for a certain class of electrolytes it has been generally reported to control the electrophoretic mobility. A knowledge of these parameters such as the zeta potential of certain ionic species under examination may be of help to predict the response speed of these ions for detection.

The foregoing description of embodiments of the invention has been given by way of example only and a number of modifications may be made without departing from the scope of the invention as defined in the appended claims. For instance, in some applications it may be possible to use the separation device without need for a cover plate over the open side of the channel.

We claim:

1. A chromatographic/electrophoretic separation and sensing device comprising a semiconductor chip mounting package carrying electrically insulated contact pins for making electrical connections with an external measurement circuit, the package supporting at least one alumina strip, said alumina strip carrying a silicon wafer body which includes a narrow longitudinal channel capable of accommodating a low volume of a sample medium for a relevant gas or liquid test process, said channel being closed on its open side by a cover plate, and said channel being associated with a first and a second electrode area being spaced from one another in the longitudinal direction of the channel such that both electrode areas are in contact with said sample medium when said sample medium is present in the channel, and each electrode area being connected to a respective contact pin of the package for integration with the said measurement circuit.

2. A device as claimed in claim 1, in which said channel has a width of 100 microns or less.

3. A device as claimed in claim 1, in which said alumina strip is secured to the mounting package by an epoxy resin adhesive material.

4. A device as claimed in claim 1, in which said silicon wafer body is secured to said alumina strip by an epoxy resin adhesive material.

5. A device as claimed in claim 1, in which each said electrode area is connected by a gold bonding wire to its contact pin.

6. A device as claimed in claim 1, in which said channel is associated with a third electrode area which is spaced form the said first and second electrode areas, said third electrode area being correspondingly connected to a contact pin.

7. A method of constructing a chromatographic/electrophoretic separation and sensing device comprising a semiconductor chip mounting package carrying electrically insulated contact pins for making electrical connectors with an external measurement circuit, the package supporting at least one alumina strip, said alumina strip carrying a silicon wafer body which includes a narrow longitudinal channel capable of accommodating a low volume of a sample medium for a relevant gas or liquid test process, said channel being closed on its open side by a cover plate, and of said channel being associated with a first and a second electrode area being spaced from one another in the longitudinal direction of the channel such that both electrode areas are in contact with said sample medium when said sample medium is present in the channel, and each electrode area being connected to a respective contact pin of the package for integration with the said measurement circuit, the method comprising the step of providing a body of silicon wafer material, and cutting a narrow longitudinal channel in said body by a micromechanical machining operation.

8. A method constructing a chromatographic/electrophoretic separation and sensing device comprising a semiconductor chip mounting package carrying electrically insulated contact pins for making electrical connections with an external measurement circuit, the package supporting one or more alumina strips, each alumina strip carrying a silicon wafer body which includes a narrow longitudinal channel capable of accommodating a low volume of a sample medium for a relevant gas or liquid test process, said channel being closed on its open side by a cover plate, and of said channel being associated with a first and a second electrode area being spaced from one another in the longitudinal direction of the channel such that both electrode areas are in contact with said sample medium when said sample medium is present in the channel, and each electrode area being connected to a respective contact pin of the package for integration with the said measurement circuit, the method comprising the step of forming the required electrode areas as metal layers deposited by an integrated circuit metallisation process.

* * * * *